United States Patent [19]

Gupton et al.

[11] Patent Number: 5,208,342

[45] Date of Patent: May 4, 1993

[54] CONVERSION OF PYRIDINE-2,3-DICARBOXYLIC ACID ESTERS TO CYCLIC ANHYDRIDES

[75] Inventors: B. Franklin Gupton, Virginia Beach, Va.; John Saukaitis, East Greenwich, R.I.

[73] Assignee: Hoechst Celanese Corporation, Somerville, N.J.

[21] Appl. No.: 860,093

[22] Filed: Mar. 30, 1992

[51] Int. Cl.$^5$ .......................................... C07D 491/048
[52] U.S. Cl. .................................... 546/116; 546/321; 203/72
[58] Field of Search ................... 546/321, 116; 203/72

[56] References Cited

FOREIGN PATENT DOCUMENTS 2192877  1/1988  United Kingdom .

Primary Examiner—Bernard Dentz

[57] ABSTRACT

In one embodiment this invention provides a process for converting a pyridine-2,3-dicarboxylic acid diester to the corresponding cyclic anhydride directly, without any recovery and purification of the pyridine-2,3-dicarboxylic acid intermediate.

An important aspect of the invention process is the utility of pure pyridine-2,3-dicarboxylic acid diester starting matter. A procedure for providing pure diester starting material is demonstrated.

11 Claims, No Drawings

CONVERSION OF PYRIDINE-2,3-DICARBOXYLIC ACID ESTERS TO CYCLIC ANHYDRIDES

BACKGROUND OF THE INVENTION

Pyridine-2,3-dicarboxylate esters are useful intermediates for the preparation of herbicidal 2-(2-imidazolin-2-yl)nicotinic acids, esters and salts, such as those described in U.S. Pat. Nos. 4,562,257; 4,638,068; and 4,647,301.

One procedure for preparing herbicidal 2-(2-imidazolin-2-yl)nicotinic acids from pyridine-2,3-dicarboxylic acid esters is illustrated by the following flow diagram:

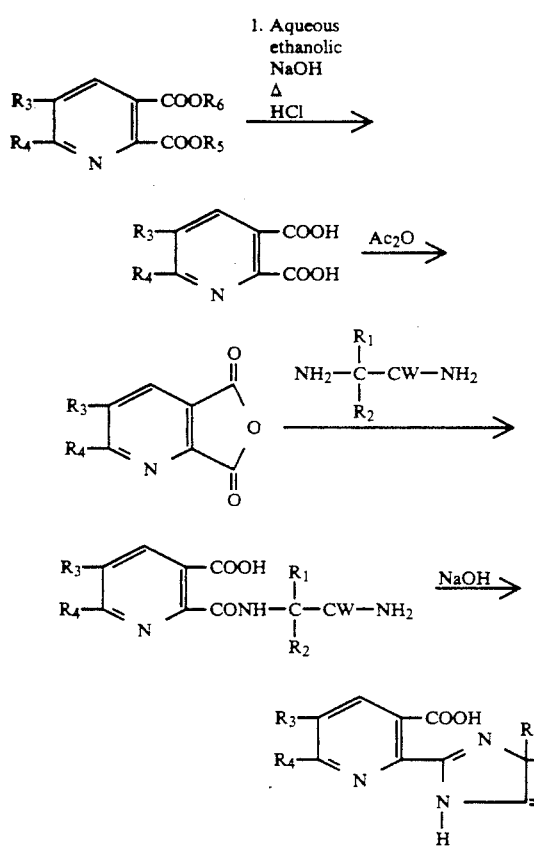

where $R^1$ is $C_1$-$C_4$ alkyl, $R_2$ is $C_1$-$C_4$ alkyl or $C_3$-$C_6$ cycloalkyl, and when $R_1$ and $R_2$ are taken together with the carbon to which they are attached they may represent $C_3$-$C_6$ cycloalkyl optionally substituted with methyl; W is O or S; and $R_3$ and $R_4$ are hydrogen, halogen, $C_1$-$C_6$ straight or branched alkyl, alkenyl, or phenyl optionally substituted; and $R_5$ and $R_6$ are each $C_1$-$C_4$ alkyl.

The preparation of pyridine-2,3-dicarboxylate esters is accomplished in accordance with various synthesis procedures, such as those described in U.S. Pat. Nos. 4,723,011; 4,798,619; and 5,047,542. The described synthesis methods involve the reaction of selected substituted compounds to form a pyridine ring structure having dicarboxylate and other substituents. Illustrative of a synthesis method is the reaction of an α-halo-β-ketoester with an α,β-unsaturated aldehyde or ketone in the presence of an ammonium salt. Another synthesis method is by the reaction of 2-aminomaleic acid diester with 2-ethacrolein. A preferred synthesis method is via the reaction of dialkyl N-hydroxyaspartate and a ketone such as 2-ethacrolein as illustrated in Example V of the present specification.

All of the synthetic methods for the production of pyridine-2,3-dicarboxylic acid diesters have in common expensive starting materials, and the subsequent recovery of impure diester product mixtures. Additional product loss is suffered when the diester is hydrolyzed to the corresponding diacid, and the diacid then is recovered and purified before conversion to the desired cyclic anhydride intermediate.

It is noted that Example 1 of U.S. Pat. No. 4,723,011 describes a procedure which is stated to yield 95% diethyl 5-ethylpyridine-2,3-dicarboxylate. All subsequent efforts to duplicate the Example 1 product purity were not successful. In any event, the utility of silica gel column chromatography as a purification procedure is not amenable to commercial-scale operation.

Because of the commercial importance of herbicidal 2-(2-imidazolin-2-yl)nicotinic acid compounds, there is intense interest in new and improved methods of synthesizing pyridine-2,3-dicarboxylic acid diesters, and converting the diesters to the corresponding cyclic anhydrides, with a view to the significant economic consequences.

Accordingly, it is an object of this invention to provide a process for the conversion of a pyridine-2,3-dicarboxylic acid diester to the corresponding cyclic anhydride without isolation and purification of the diacid intermediate.

It is a further object of this invention to provide a process for preparing a pyridine-2,3-dicarboxylic acid diester with a purity of at least about 90 weight percent, and converting the pure diester to the corresponding cyclic anhydride without recovery and purification of the diacid intermediate.

Other objects and advantages of the present invention shall become apparent from the accompanying description and examples.

DESCRIPTION OF THE INVENTION

One or more objects of the present invention are accomplished by the provision of a process for the production of a pyridine-2,3-dicarboxylic anhydride compound which comprises (1) hydrolyzing a pyridine-2,3-dicarboxylic diester of at least 90 weight percent purity in an alkaline aqueous medium, and acidifying the reaction medium to form a corresponding pyridine-2,3-dicarboxylic acid having the formula:

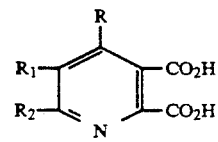

where each of R, $R_1$ and $R_2$ is hydrogen, halogen, $C_1$-$C_6$ alkyl, phenyl or $C_1$-$C_4$ alkyl-substituted phenyl group; (2) extracting the aqueous reaction medium with an organic solvent to obtain a solvent solution of the pyridine-2,3-dicarboxylic acid; (3) removing any residual water by azeotropic distillation; and (4) reacting the pyridine-2,3-dicarboxylic acid with at least an equimolar quantity of alkanoic anhydride in an organic solvent medium under anhydrous conditions to form pyridine-2,3-dicarboxylic anhydride product.

In another embodiment this invention provides a process for the production of a pyridine-2,3-dicarboxylic anhydride compound which comprises (1) synthesizing and recovering a pyridine-2,3-dicarboxylic diester which contains more than about 10 weight percent of organic impurities, and which corresponds to the formula:

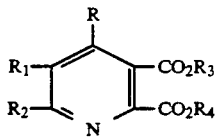

where each of R, $R_1$ and $R_2$ is hydrogen, halogen, $C_1$–$C_6$ alkyl, phenyl or $C_1$–$C_4$ alkyl-substituted phenyl group, and each of $R_3$ and $R_4$ is a $C_1$–$C_{12}$ organic group; (2) cycling the diester through a thin film evaporator and distillation column system to provide a diester distillate of at least 90 weight percent purity; (3) hydrolyzing the purified diester in an alkaline aqueous medium, and acidifying the reaction medium to form a corresponding pyridine-2,3-dicarboxylic acid having the formula:

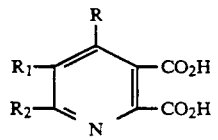

where R, $R_1$ and $R_2$ are as previously defined; (4) extracting the aqueous reaction medium with an organic solvent to obtain a solvent solution of the pyridine-2,3-dicarboxylic acid; (5) removing any residual water by azeotropic distillation; and (6) reacting the pyridine-2,3-dicarboxylic acid with at least an equimolar quantity of alkanoic anhydride in an organic solvent medium under anhydrous conditions to form pyridine-2,3-dicarboxylic anhydride product.

An important aspect of the present invention is the provision of a pyridine-2,3-dicarboxylic acid diester of at least 90 weight percent purity.

Pyridine-2,3-dicarboxylic acid diesters typically are prepared from reactants which form a substituted pyridine ring structure. Usually a recovered crude diester product contains in the range of 20–50 weight percent of impurities and byproducts.

The impure pyridine-2,3-dicarboxylic acid diester is converted to a cyclic anhydride product via diacid intermediate formation. Typically the crude diacid intermediate is recovered and subjected to a purification procedure. The pure diacid then is converted to a cyclic anhydride, and the anhydride reacted with a reagent such as 2-amino-2,3-dimethylbutyronitrile to form a 2-(2-imidazolin-2-yl)nicotinic acid type of herbicide product.

The practice of the present invention provides important advantages with respect to the conversion of a pyridine-2,3-dicarboxylic acid diester to a corresponding cyclic anhydride. It is not necessary to recover and purify the diacid intermediate, since the present invention provides the diacid intermediate in pure form without isolation.

Because of economic considerations, it is desirable to have a means for purifying pyridine-2,3-dicarboxylic acid diester which is suitable for commercial-scale operation. Example VII of the present specification demonstrates that a large volume production of pyridine-2,3-dicarboxylic acid diester (>90% purity) can be achieved by cycling the diester through a thin-film evaporation and distillation system. A two-pass procedure yields the diester with the required level of high purity.

In the present invention process, the pure diester is hydrolyzed in an aqueous alkaline medium to form a diacid salt intermediate and the alcohol of the corresponding diester.

The alkalinity of the diester hydrolysis medium can be provided by basic alkali metal or alkaline earth metal compounds, such as hydroxides and carbonates of sodium, potassium, lithium, calcium and magnesium.

Prior to acidification, the alcohol component formed by diester hydrolysis is removed by distillation. The subsequent acidification step can be accomplished by adding a measured quantity of inorganic or organic acid to the hydrolysis medium to convert the diacid salt intermediate to a diacid intermediate. Suitable acidic reagents include hydrochloric acid, sulfuric acid, nitric acid, phosphoric acid, and the like.

After the formation of the diacid intermediate, the aqueous reaction medium is extracted with an organic solvent to obtain a solvent solution of the pyridine-2,3-dicarboxylic acid intermediate. Organic solvents suitable for the extraction step include diethyl ether, ethyl acetate, nitromethane, methylenedichloride, toluene, xylene, chlorobenzene, nitrobenzene, tetrahydrofuran, butanol, cyclohexanol, and the like.

The organic solvent solution of the diacid intermediate preferably is subjected to distillation to remove volatiles such as the alcohol byproduct of the hydrolysis step, and optionally to remove part or all of the organic solvent. It is essential that all residual water is removed from the diacid intermediate medium. It is convenient and practical to add an organic solvent (e.g., toluene) which forms an azeotrope with water under distillation conditions, and thereby completely remove the residual water content.

The resultant anhydrous diacid intermediate medium then is treated with an alkanoic anhydride such as acetic anhydride, in at least a stoichiometric quantity. Preferably, the formation of pyridine-2,3-dicarboxylic anhydride is conducted in an organic solvent medium in the presence of an aprotic basic amine compound at a temperature between about 10°–40° C.

Aprotic basic amine compounds are illustrated by triethylamine, pyridine, 2-picoline, 4-picoline and quinoline. The amine compound has a catalytic effect on the cyclic anhydride-forming reaction. The presence of the amine compound has additional advantage for subsequent conversion of the pyridine-2,3-dicarboxylic anhydride to a 2-(2-imidazolin-2-yl)nicotinic acid derivative, since it enhances the interaction of the cyclic anhydride with a reactant such as 2-amino-2,3-dimethylbutyronitrile, and favors the formation of the desired 2-carbamoylnicotinic acid isomer.

The anhydrous pyridine-2,3-dicarboxylic anhydride solution product of the present invention process can be utilized directly for the synthesis of the commercially important herbicidal 2-carbamoylnicotinic acid derivatives described herein.

The present invention process has important economic advantages for purposes of commercial-scale operation. Because the diacid intermediate is not isolated during the process stages, the operational equipment units normally utilized for crystallization, filtering and drying of the diacid intermediate are eliminated. The process can be practiced in shorter cycle times with increased productivity. Higher yields are obtained and waste disposal is minimized because there is no formation of a crystallization mother liquor.

The following examples are further illustrative of the present invention. The components and specific ingredients are presented as being typical, and various modifications can be derived in view of the foregoing disclosure within the scope of the invention.

EXAMPLE I

This Example illustrates the preparation of diethyl 5-ethylpyridine-2,3-dicarboxylate (5-EPDC) from diethyl oxalacetate, 2-ethacrolein and ammonium sulfamate.

To a liter 3-neck Morton flask fitted with a thermowatch, reflux condenser, and motor-driven stirrer is added 94.0 g (0.5 mol) of distilled diethyl oxalacetate, 68.4 g (0.6 mol) of ammonium sulfamate, and 200.0 g of methanol. The mixture is brought to reflux and held for 30 minutes, followed by the dropwise addition of 58.8 g (0.7 mol) of distilled 2-ethacrolein over 30 minutes. The reflux temperature is maintained for an additional hour, followed by cooling to about 10° C. and filtration.

A yield of 46.19 g of diethyl 5-EPDC is obtained, as determined by gas chromatography, employing octanol as an internal standard as pure diethyl 5-ethylpyridine-2,3-dicarboxylate as an external reference standard.

EXAMPLE II

This Example illustrates the preparation of dimethyl 6-phenylpyridine-2,3-dicarboxylate from dimethyl 2-aminomaleate and phenyl ethynyl ketone.

A suspension of 3.18 g (20 mmols) of dimethyl 2-aminomaleate and 2.6 g (20 mmols) of phenyl ethynyl ketone in 10 mL of methanol is heated at reflux for 20 hours. The methanol is removed in vacuo, and the residue is digested in ether and filtered to give 2.52 g of the diester product as a tan solid, mp 124°-127° C.

EXAMPLE III

This Example illustrates the preparation of diethyl 5-ethylpyridine-2,3-dicarboxylate from diethyl 3-chloro-2-oxo-butanedicarboxylate, 2-ethacrolein and ammonium sulfamate.

A stirred mixture of 2-ethacrolein (4.2 g, 0.05 mol), diethyl 3-chloro-2-oxo-butanedioate, (11.2 g, 0.05 mol) and ammonium sulfamate, (15.4 g, 0.135 mol) in ethanol (37 mL) is heated at reflux. After 15 hours the mixture is cooled to room temperature and the solvent removed by distillation under reduced pressure. The residue is treated with water and extracted with ethyl acetate. The organic phase is separated and concentrated in vacuo, and the residual product is recovered.

EXAMPLE IV

This Example illustrates the preparation of diethyl 5-ethylpyridine-2,3-dicarboxylate from diethyl 2-aminomaleate and 2-ethacrolein.

Acetic acid (10 mL) is added to a solution of diethyl 2-aminomaleate (18.7 g, 0.10 mol) in ethanol (38 mL) in a 250 mL flask (pH, 3.9). The reaction flask is equipped with a reflux condenser, thermometer, heating mantle, stirrer, and dropping funnels. 2-Ethacrolein (12.8 g, 0.13 mol) is added to the flask contents, and the reaction mixture is heated at reflux for 4 hours. The solvent is removed on a vacuum rotary evaporator, and the residue is recovered (13.8 g).

EXAMPLE V

This example illustrates the preparation of diethyl 5-ethylpyridine-2,3-dicarboxylate from diethyl N-hydroxyaspartate and 2-ethacrolein.

Diethyl N-hydroxyaspartate (20.2 g, 0.1 mol) is dissolved in benzene (100 mL) and stirred under nitrogen. Trifluoroacetic acid (2.0 g, 0.018 mol) and 2-ethacrolein (9.8 g, 0.11 mol) are added, and the reaction mixture is stirred at 72°-75° C. for 16 hours. The reaction mixture is concentrated under reduced pressure to obtain crude diethyl 5-EPDC (27.92 g). Gas-liquid chromatographic (GLC) analysis of the product indicates that the reaction had proceeded with 91% conversion (based on diethyl maleate) and 41% yield (based on external standard) to diethyl 5-EPDC.

EXAMPLE VI

This Example illustrates the preparation of diethyl 5-ethylpyridine-2,3-dicarboxylate from diethyl maleate, 2-ethacrolein and hydroxylamine sulfate.

A solution of 394.4 g (0.60 mol; 1.20 eq) of 25% aqueous hydroxylamine sulfate is charged to a 2-liter round-bottom flask equipped with a reflux condenser, thermometer, dropping funnel, mechanical stirrer, and cooling bath. Over about a thirty minute period, 94.1 g (1.20 mols) of 50% aqueous sodium hydroxide is added to the flask contents. Phenolphthalein indicator is added, and additional caustic is added dropwise to a pH endpoint of 9.5. The temperature is maintained below 40° C. A 400 mL quantity of ethanol then is added, and precipitated sodium sulfate is removed by filtration. This is followed by the addition of 172.0 (1 mol) of diethyl maleate, and the resulting homogeneous solution is stirred for 30 minutes.

Acetic acid (125 mL) is added to lower the pH from 6.76 to 4.1, then 122.5 g (1.3 mol of 90% purity) of 2-ethacrolein is added at room temperature over a 30 minute period. The mixture is heated to 80° C. and stirred for 20 hours. The diethyl 5-EPDC yield is 48.8%.

EXAMPLE VII

This Example illustrates the purification of diethyl 5-ethylpyridine-2,3-dicarboxylate (diethyl 5-EPDC) synthesized in accordance with the Example V procedure, utilizing a thin-film evaporator and distillation column system following a two-pass procedure.

PURIFICATION SYSTEM

1. Diethyl 5-EPDC feed material (55% purity) was charged into a 60 gallon S.S feed kettle equipped with a dual paddle agitator.
2. Feed material was gravity fed through a ¼" Strahman ram-type valve and ⅜" OD. S.S. feed lines to the suction side of a 3-gear positive displacement Zenith metering pump.
3. The pump was driven by a ¼ HP U.S. Varidrive motor coupled to a Parajust voltage regulator, which controlled the speed of the pump and the feed rate.
4. The equipment arrangement for a two-pass procedure was as follows:
   a. Pumped feed flowed through ⅜" OD S.S. feed lines and was flashed across a ¼" Milton Roy diaphragm back pressure valve to the base of a steam heated rising film evaporator having 1.96 sq. ft. of heat transfer area.
b. Hot feed exiting the rising film evaporator was fed to the midsection of a packed distillation column.
c. The distillation column had four feet of a mesh type low pressure drop Goodloe S.S. packing in both the stripping and rectification sections.
d. The reboiler for the distillation column was an Artisan horizontal thin film Rototherm Evaporator. The heating medium flowing through the Rototherm's jacket (0.88 sq. ft. HTA, #47787A) was Syltherm 800.
e. Bottoms material was removed from the system via a 2" Hills-McCanna ball valve.
f. Vapor rose through the column, passed a swing funnel type reflux splitter and was condensed on the tube side of a shell and tube condenser having 22.0 sq. ft. of heat transfer area. Chilled glycol served as the cooling medium.
5. Condensed liquid was either removed from the system as distillate or returned to the column as reflux liquids. The division of distillate and reflux liquid was controlled by an Artisan microcomputer.
6. Uncondensed vapors bypassing the primary condenser at the top of the rectification column were condensed by two dry ice/acetone cold traps in series.
7. Temperatures were recorded using Type J thermocouples and read directly off a Beckman digital readout.
8. System pressures were read using a McLeod Stokes vacuum gauge.
9. System vacuum was provided by a KTC-60 Kinney vacuum pump.

PURIFICATION PROCEDURE

1. The following system parameters were established for the first pass runs:
   a. Feed rates varied from 39.44 to 74.13 pph.
   b. % evaporation ranged from 6.98 to 24.30%.
   c. The reflux ratio was 2 or 1.
   d. The system pressure read at the top of the column, middle of the column (6" above the feed point and into the packing) and bottom of the column had highs of 15, 17 and 25 mm Hg and lows of 14, 15 and 17.5 mm Hg respectively.
2. The following system parameters were established for the second pass runs:
   a. Feed rates varied from 11.91 to 37.98 pph.
   b. % evaporation ranged from 35.71 to 56.68%.
   c. The reflux ratio was 1.
   d. The system pressure read at the top of the column, middle of the column, and bottom of the column has highs of 5, 9 and 12 mm Hg and lows of 0.9, 4.5 and 5 mm Hg respectively.
3. Feed material for second pass runs were first pass bottoms generated in the first pass runs.

Four purification runs are summarized in the Table. The final diethyl 5-EPDC product after a second-pass procedure was 91%, and the recovery of product was about 95%. The purity of the product after first pass runs did not exceed 70%.

TABLE

| | Run No. | | | |
|---|---|---|---|---|
| | 1 | 2 | 3 | 4 |
| | First Pass | | Second Pass | |
| Temperatures (f) | | | | |
| 1) Feed | 73.9 | 72.7 | 90.5 | 89.8 |
| 2) Flash | 73.1 | 73.4 | 76.6 | 79.0 |
| 3) Evaporator Exit | 355.0 | 348.2 | 359.8 | 358.6 |
| 4) Rototherm Bottoms | 425.7 | 430.3 | 482.6 | 479.0 |
| 5) Bottom Tee Vapor | 422.4 | 427.8 | 397.1 | 410.1 |
| 6) Column Vapor (¼ ft) | 419.8 | 425.7 | 386.1 | 395.5 |
| 7) Column Vapor (2 ft) | 414.2 | 416.8 | 356.0 | 355.5 |
| 8) Column Vapor (3 ft) | 409.7 | 411.2 | 357.3 | 356.7 |
| 9) Column Vapor (5 ft) | 375.1 | 369.4 | 240.7 | 39.5 |
| 10) Column Vapor (6 ft) | 367.4 | 353.6 | 335.2 | 333.8 |
| 11) Reflux Vapor | 194.3 | 196.5 | 288.6 | 287.6 |
| 12) Reflux Liquid | 93.3 | 122.7 | 287.6 | 286.6 |
| 13) Condenser Vent Vapor | 43.6 | 38.5 | 64.2 | 65.2 |
| 14) Distillate | 58.4 | 61.8 | 161.0 | 137.6 |
| 15) Evaporator Steam In | 360.5 | 359.9 | 362.6 | 361.1 |
| 16) Evaporator Steam Out | 358.2 | 359.7 | 359.1 | 358.0 |
| 17) Process Oil In | 459.2 | 467.2 | 518.2 | 507.1 |
| 18) Process Oil Out | 458.2 | 466.3 | 516.1 | 504.8 |
| 19) Condenser Glycol In | 13.6 | 12.0 | 57.0 | 57.0 |
| 20) Condenser Glycol Out | 22.4 | 21.8 | 57.1 | 56.9 |
| System Parameters | | | | |
| Feed Rates (pph) | 45.27 | 74.13 | 11.91 | 13.63 |
| % Evaporation | 12.19 | 13.39 | 56.68 | 51.46 |
| Reflux Ratio | 2 | 1 | 1 | 1 |
| System Pressure (mm Hg): | | | | |
| a) Top of Rect. Column | 15.0 | 15.0 | 1.0 | 1.0 |
| b) Bottom of Rect. Column | 16.0 | 17.0 | 4.0 | 4.5 |
| c) Bottom of Strip. Column | 19.0 | 19.0 | 5.0 | 5.0 |

EXAMPLE VIII

This Example illustrates the conversion of purified diethyl- 5-ethylpyridine-2,3-dicarboxylate to the corresponding cyclic anhydride in accordance with the present invention.

A reaction flask with a reflux condenser is charged with 111.0 g of 25% sodium hydroxide. The aqueous medium is heated to 55° C. and a 56.2 g quantity of diethyl 5-ethylpyridine-2,3-dicarboxylate (91.2% purity) is added dropwise with stirring over a 15 minute period. The reaction medium is heated at 65° C. for an additional 15 minutes.

Ethanol-water is distilled from the reaction medium under reduced pressure (120 mm Hg), then 70 g of water and 318 g of tetrahydrofuran are added to the flask contents which are at a temperature of 40° C. The pH of the reaction medium is adjusted to 1.65 with 50% sulfuric acid. The aqueous phase is separated from the organic medium. The tetrahydrofuran is distilled from the organic medium to a reaction flask temperature of 90° C.

A Dean-Stark apparatus is attached to the reaction flask, and toluene (300 g) is added to the flask contents. A toluene-water azeotrope is distilled under slightly reduced pressure at a temperature of 70°-75° C.

Acetic anhydride (50.4 g) and 4-picoline (19.1 g) are added to the reaction flask contents at room temperature. All of the solids suspended in the reaction medium dissolve to form a brown solution. A slight exotherm (3° C.) is observed as the solution is stirred over a 30 minute period. Analysis of the reaction medium indicates a 74% yield of cyclic anhydride product.

The resultant cyclic anhydride solution is added dropwise to a stirred solution of 2-amino-2,3-dimethylbutyronitrile (0.15 mol) and 4-picoline (1.2 mol) in toluene, while maintaining the temperature at 10°-12° C. The reaction medium is stirred for one hour at 10°-12° C. Analysis of the reaction medium by high performance chromatography indicates a yield of about 88% of 2-[(1-cyano-1,2dimethylpropyl)carbamoyl]-5-ethylnicotinic acid.

Following the procedure described in U.S. Pat. No. 4,562,257, the nicotinic acid solution is treated with aqueous sodium hydroxide at 40° C., and the resultant 2-(4-isopropyl-4-methyl-5-oxo-2-imidazolin-2-yl)-5-ethylnicotinic acid is recovered for utility as a herbicide product.

What is claimed is:

1. A process for the production of a pyridine-2,3-dicarboxylic anhydride compound which comprises (1) synthesizing and recovering a pyridine-2,3-dicarboxylic diester which contains more than about 10 weight percent of organic impurities, and which corresponds to the formula:

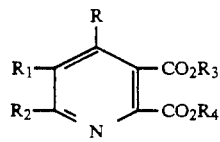

where each of R, $R_1$ and $R_2$ is hydrogen, halogen, $C_1$–$C_6$ alkyl, phenyl or $C_1$–$C_4$ alkyl-substituted phenyl group, and each of $R_3$ and $R_4$ is a $C_1$–$C_{12}$ organic group; (2) cycling the diester through a thin film evaporator and distillation column system to provide a diester distillate of at least 90 weight percent purity; (3) hydrolyzing the purified diester in an alkaline aqueous medium, and acidifying the reaction medium to form a corresponding 2,3-pyridine-dicarboxylic acid having the formula:

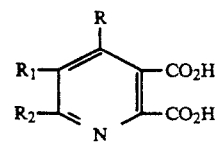

where R, $R_1$ and $R_2$ are as previously defined; (4) extracting the aqueous reaction medium with an organic solvent to obtain a solvent solution of the pyridine-2,3-dicarboxylic acid; (5) removing any residual water by azeotropic distillation; and (6) reacting the pyridine-2,3-dicarboxylic acid with at least an equimolar quantity of alkanoic anhydride in an organic solvent medium under anhydrous conditions to form pyridine-2,3-dicarboxylic anhydride product.

2. A process in accordance with claim 8 wherein the diester synthesis in step(1) involves a pyridine ring-forming reaction.

3. A process in accordance with claim 1 wherein the step(1) diester is a $C_1$–$C_6$ dialkyl ester.

4. A process in accordance With claim 1 wherein the pyridine-2,3-dicarboxylic formula R and $R_2$ are hydrogen, and $R_1$ is $C_1$–$C_6$ alkyl, phenyl or $C_1$–$C_4$ alkyl-substituted phenyl group.

5. A process in accordance with claim 1 wherein the extraction organic solvent in step(4) is tetrahydrofuran.

6. A process in accordance with claim 1 wherein the azeotropic distillation medium in step(5) is toluene.

7. A process in accordance with claim 1 wherein the alkanoic anhydride in step(6) is acetic anhydride.

8. A process in accordance with claim 1 wherein the reaction medium in step(6) contains an aprotic basic amine compound.

9. A process in accordance with claim 1 wherein the anhydride forming reaction in step(6) is conducted at a temperature between about 10°–40° C.

10. A process in accordance with claim 1 wherein the product of the process is 5-ethylpyridine-2,3-dicarboxylic acid anhydride.

11. A process in accordance with claim 1 wherein the product of the process is 5-phenylpyridine-2,3-dicarboxylic acid anhydride.

* * * * *